United States Patent [19]

Konrad et al.

[11] Patent Number: 4,704,474
[45] Date of Patent: Nov. 3, 1987

[54] 1,4-DIAMINO-5-CHLORO-2-NITROBENZENE DERIVATIVES, PROCESSES FOR THEIR PRODUCTION AND COMPOSITIONS CONTAINING THE SAME FOR THE COLORATION OF HAIR

[75] Inventors: Eugen Konrad, Darmstadt; Thomas Clausen, Weiterstadt, both of Fed. Rep. of Germany

[73] Assignee: Wella Aktiengesellschaft, Darmstadt, Fed. Rep. of Germany

[21] Appl. No.: 834,644

[22] Filed: Feb. 26, 1986

Related U.S. Application Data

[63] Continuation of Ser. No. 625,115, Jun. 27, 1984, abandoned.

[30] Foreign Application Priority Data

Jun. 28, 1983 [DE] Fed. Rep. of Germany ....... 3323207

[51] Int. Cl.$^4$ .................... C07C 87/60; A61K 7/13
[52] U.S. Cl. ........................ 564/441; 8/407; 8/415
[58] Field of Search ............... 564/441; 8/407, 415

[56] References Cited

U.S. PATENT DOCUMENTS

| | | | |
|---|---|---|---|
| 3,274,249 | 9/1966 | Brunner et al. | 564/441 |
| 3,973,900 | 8/1976 | Husemeyer et al. | 8/415 |
| 4,470,826 | 9/1984 | Bugant et al. | 564/441 |

FOREIGN PATENT DOCUMENTS

| | | |
|---|---|---|
| 1017750 | 7/1959 | Fed. Rep. of Germany . |
| 2157844 | 5/1973 | Fed. Rep. of Germany .......... 8/415 |

OTHER PUBLICATIONS

J. C. Johnson, "Hair Dyes" Noyes Corp. Park Ridge (USA) (1973) pp. 1-91, 113-139.
E. Saragin, "Cosmetics", Science Technology (1957) Interscience Publishers Inc., New York, pp. 503-515.
H. Janistyn, "Handbuch der Kosmetica und Reischstoffe" (1973) pp. 378-406.
Ames, B. N. et al, "Methods for Detecting Carcinogens and Mutagens with Salmonella Mammalian-Microsome Mutagenicity Test", *Mutation Research* vol. 31, pp. 347-364 (1975).
Balsam, M. S. et al, *Cosmetics, Science and Technology*, vol. 2 p. 297 (1972).

*Primary Examiner*—Charles F. Warren
*Assistant Examiner*—John A. Sopp
*Attorney, Agent, or Firm*—Michael J. Striker

[57] ABSTRACT

New 1,4-diamino-5-chloro-2-nitrobenzene derivatives are disclosed of the formula I

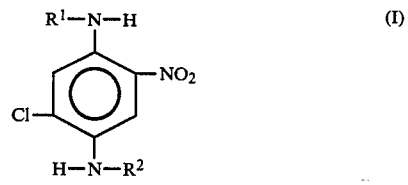

Wherein $R^1$ and $R^2$ are the same or different and are each hydrogen, 2-hydroxyethyl or 2,3-dihydroxypropyl, with the proviso, that at least one of said $R^1$ and $R^2$ is 2,3-dihydroxypropyl, along with processes for their production, as well as hair coloring compositions containing the same and methods of coloring hair. The compounds are red- to violet-coloring direct dyes, and are readily soluble in water, with favorable toxicological characteristics.

20 Claims, No Drawings

1,4-DIAMINO-5-CHLORO-2-NITROBENZENE DERIVATIVES, PROCESSES FOR THEIR PRODUCTION AND COMPOSITIONS CONTAINING THE SAME FOR THE COLORATION OF HAIR

This application is a continuation of application Ser. No. 625,115, filed June 27, 1984, now abandoned.

BACKGROUND OF THE INVENTION

The present invention involves compositions for the dyeing of hair with nitro dyes, whereby new derivatives of 1,4-diamino-5-chloro-2-nitrobenzene are employed, as well as a process for the production of these derivatives and methods for the use thereof.

Nitro dyes have acquired an essential importance in the field of hair coloring. Through combination of various nitro dyes coloring compositions can be prepared which make possible the dyeing of hair into natural and popular, so-called "mod" (i.e. modern) tones, without the addition of oxidation means. The nitro dyes are likewise important components of oxidation hair coloring compositions, since they make it possible in simple manner to produce natural or mod nuances.

Numerous particular requirements are placed on nitro dyes that are employed for the coloring of human hair. Thus they must be non-harmful both from a toxicological and dermatological point of view, and make it possible to obtain colorations of a desired intensity, a prerequisite for which among others is also a sufficient water-solubility. Additionally required for the obtained hair colorations are good light, acid and friction fastness. It is moreover a prerequisite for their employment in oxidation hair dyeing compositions that they remain stable in the presence of hydrogen peroxide in ammoniacal solution.

For some time now, in addition to others, derivatives of o- and p-phenylene-diamine, e.g. the yellow dye 4-nitro-o-phenylenediamine or the red 2-nitro-p-phenylenediamine have been employed as nitro dyes in hair coloring compositions. However, these dyes do not fulfill the above mentioned conditions, in particular the physiological prerequisites, to a satisfactory extent.

5-chloro-2-nitro-p-phenylenediamine derivatives, which better fulfill these prerequisites, are known from DE-PS No. 2 157 844. A disadvantage of the disclosed compounds is their relatively low water-solubility, which hinders employment in higher concentrations for the obtaining of greater deepness of color.

SUMMARY OF THE INVENTION

It is therefore an object according to the present invention to avoid the above mentioned disadvantages of the known hair coloring compounds.

It is a further object according to the new invention to be able to provide hair colorations in pure red to violet color tones of suitable stability.

An additional object according to the present invention is to provide dyes of this type that are better soluble in water.

Finally, it is an object according to the present invention to make available a composition for the dyeing of hair which can be employed without the addition of oxidation means or, on the other hand, of the type with which the addition of oxidation means is necessary.

It has been discovered according to the present invention that the above mentioned disadvantages are eliminated through the use of hair coloring compositions with a content of 1,4-diamino-5-chloro-2-nitrobenzene derivatives of the formula I

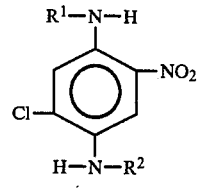

wherein $R^1$ and $R^2$ are the same or different and are each hydrogen, 2-hydroxyethyl or 2,3-dihydroxypropyl, with the proviso that at least one of said $R^1$ and $R^2$ is 2,3-dihydroxypropyl.

These dyes are new and provide hair colorations in pure red to violet color tones of outstanding stability. Their preparation can follow according to either of two different pathways. Thus, on the one hand, the compounds of formula I can be obtained proceding from 1,4-diamino-5-chloro-2-nitrobenzene, which, if necessary, can be substituted at one or both amino groups with a 2-hydroxyethyl group, by means of reaction with chloropropanediol-(2,3) in alkaline medium. The other pathway is as follows: proceding from 5-acetylamino-2,4-dichloronitrobenzene, a chlorine atom is exchanged nucleophilically for the amino group by 1-aminopropanediol-(2,3) and thereafter the acetyl group saponified, whereby the free amino group, if necessary, can still be ethoxylated thereafter. The production of the starting materials, namely the 1,4-diamino-5-chloro-2-nitrobenzene, hydroxy ethylated 1,4-diamino-5-chloro-2-nitrobenzene derivatives and the 5-acetylamino-2,4-dichloronitrobenzene, is known, and is described, for example, in the already mentioned DE-PS No. 2 157 844, which is hereby incorporated by reference.

The dyes according to the present invention of formula I are more water-soluble than the dyes according to German Pat. No. 2 157 844. In surprising manner they also display more favorable characteristics from the toxicological point of view and in the Ames test with regard to their mutagenic activity than the dyes according to the above mentioned DE-PS No. 2 157 844.

The composition according to the present invention for the dying of hair involves not only those which are employed without the addition of oxidation means, but also those with which the addition of oxidation means is necessary.

The first mentioned hair coloring compositions without oxidation means addition involves those which, in addition to the dyes of the above given formula, can contain still other dyes that are direct-drawing on the hair. Of these dyes known for hair coloration, the following classes may be mentioned by way of example: Aromatic nitro dyes (e.g. 1,2-diamino-4-nitrobenzene), azo dyes (e.g. Acid Brown 4, C.I. 14 805), anthraquinone dyes (e.g. Disperse Violet 4, C.I. 61 105), triphenylmethane dyes (e.g. Basic Violet 1, C.I. 61 100), whereby the dyes of these classes, indeed according to the type their substitutions, can have acid, non-ionogenic or basic character. Further suitable dyes direct-drawing on the hair are described for example in the book by J. C. Johnson, "Hair Dyes" Noyes Data Corp. Park-Ridge (USA) (1973).

Hair coloring compositions which contain mixtures of such dyes can provide, in addition to pure mod tones, also fashioable blonde and brown tones of outstanding stability.

The form of preparation for the described hair coloring compositions based on dyes direct-drawing on the hair include, for example, a solution, in particular an aqueous or aqueous-alcoholic solution. Preferred forms of preparation include, moreover, a creme, a gel or an emulsion, whereby they can also be sprayed as a mixture with a propellant gas or by means of a pump.

The dyes of formula I should be contained in these hair coloring compositions in a concentration from about 0.01 up to 2.0 percent by weight, preferably from 0.01 up to 1.0 percent by weight. The total content of dyes should generally lie within the limits from about 0.01 up to 3.0 percent by weight.

The pH-value of these coloring compositions lies within the range from 7 to 10.5, in particular at pH 7.5 up to 9.5, whereby the adjustment of the desired pH-value follows mainly by means of ammonia. However, this can also be accomplished with organic amines such as for example monoethanolamine or triethanolamine.

The employment of the compositions according to the present invention follows in customary manner by means of application of the composition to the hair and allowing the same to remain in contact for a time period between 5 and 30 minutes. Subsequently the hair is rinsed with water, if necessary further with a weak organic acid, and then dried. Suitable weak organic acids for employment according to the present invention include, for example, acetic acid, citric acid, tartaric acid and the like.

The above described hair coloring compositions without oxidation means addition can obviously also contain cosmetic polymerizates, whereby along with the dyeing simultaneously a strengthening of the hair is obtained. Such compositions are generally designated tone strengtheners or color strengtheners.

Of the polymerizates known cosmetically for this purpose, mention may be made by way of example of polyvinylpyrrolidone, polyvinylacetate, polyvinylalcohol or polyacrylo-compounds such as acrylic acid or methacrylic acid, basic polymerizate of esters of both these acids and amino alcohols or their salts or quaternization products, polyacrylonitrile, polyvinyllactam as well as copolymerizates of such compounds, such as polyvinylpyrrolidol-vinylacetate and the like.

Likewise suitable for the mentioned purpose are natural polymers, such as chitosan (deacetylated chitin) or chitosan derivatives.

The polymerizates are contained in the compositions according to the present invention in customary amounts from about 1 up to 4 percent by weight. The pH-value of the compositions lies witin the range from about 6.0 up to 9.0.

Employment of these hair coloring compositions with additional strengthening follows in known and customary manner through moistening of the hair with the strengthener, fixing (setting) of the hair into a hairdo, and subsequent drying.

It is self evident that the above described hair coloring compositions without addition of oxidation means can, if necessary, contain further customary cosmetic additives such as e.g. care substances, wetting agents, thickeners, softeners and perfume oils.

As mentioned above, also belonging to the subject of the present invention are those hair coloring compositions to which an addition of oxidation means is necessary. They contain, aside from the dye according to formula I, yet additional known oxidation dyes, which require an oxidative development.

Such oxidation dyes involve mainly aromatic p-diamines and p-aminophenols such as for example p-toluylenediamine, p-phenylenediamine, p-aminophenol and similar compounds, which can be combined, for the purpose of nuancing of the colorations with typical modifiers, such as e.g. m-phenylenediamine, resorcin, m-aminophenol among others.

Such known and customary oxidation dyes for hair coloring are described, for example, in the book by E. Sagarin, "Cosmetics", Science and Technology (1957), Interscience Publishers Inc., New York, pages 503 et seq. as well as in the book by H. Janistyn, "Handbuch der Kosmetika und Reichstoffe" (1973) pages 378 et. seq.

In addition to pure mod tones, also fashioable blonde and brown tones can be obtained with mixtures of these oxidation dyes and the dyes according to formula I according to the present invention.

The dyes of formula I are contained in the hair coloring compositions with addition of oxidation means in a concentration from about 0.01 up to 2.0 percent by weight, preferably 0.05 up to 1.0 percent by weight. The total content of dye in these hair coloring compositions amounts to between 0.1 and 5.0 percent by weight.

Oxidation hair coloring compositions are generally adjusted alkaline, preferably to a pH-value from about 8.0 up to 11.5, whereby the adjustment follows in particular by means of ammonia. One can, however, also employ for this purpose other organic amines, e.g. monoethanolamine or triethanolamine. Mainly coming into consideration as oxidation means for the development of the hair dyes are hydrogen peroxide and its addition compounds. The form of preparation for this type of hair coloring composition can be the same as those described above for hair coloring compositions without oxidation means addition. Preferably, they are provided in the form of a creme or a gel.

Customary additions for cremes, emulsions or gels include, for example, solvents such as water, lower aliphatic alcohols, for example ethanol, propanol, isopropanol, glycerin or glycols such as ethyleneglycol and propyleneglycol, or even glycolethers, moreover wetting agents or emulsions from the classes of anionic, cationic, amphoteric or non-ionogenic surface-active substances such as fatty alcohol sulfate, fatty alcoholethersulfate, alkylsulfonate, alkylbenzene sulfate, alkyltrimethylammonium salt, alkylbetaine, oxethylated fatty alcohols, oxethylated nonylphenols, fatty acid alkanolamide, oxethylated fatty acid ester, moreover thickeners such as higher fatty alcohols, Bentonite, starch, polyacrylic acids, cellulosederivatives, such as carboxymethylcellulose, alginate, vaseline, paraffin oils, fatty acids as well as care substances such as lanolin derivatives, cholesterin, pantothenic acid and betaine, further perfume oils and complex formers. The mentioned components are employed in amounts custmary for such purposes, for example the wetting agents and emulsifiers in concentrations from about 0.5 up to 30 percent by weight, whereas the thickeners can be contained in the preparations in an amount from about 0.1 up to 25 percent by weight.

Employment of the mentioned preparations follows in known manner, i.e. by mixing the hair coloring composition with the oxidation means before the treatment, and then applying the mixture onto the hair.

After a working-in period sufficient for the pupposes of hair coloration, which customarily amounts to between 10 and 45 minutes, the hair is rinsed with water, if necessary further with a weak organic acid such as e.g. citric acid or tartaric acid, and then dried.

The novel features which are considered as characteristic for the invention are set forth in particular in the appended claims. The invention itself, however, both as to its construction and its method of operation, together with additional objects and advantages thereof, will be best understood from the following description of specific embodiments.

EXAMPLES OF COSMETIC COMPOSITIONS

Example 1

A liquid hair coloring composition with the following ingredients:

| | |
|---|---|
| 0.2 g | 1-amino-4-(2',3'-dihydroxypropyl)-amino-5-chloro-2-nitrobenzene |
| 0.5 g | hydroxyethyl cellulose |
| 5.0 g | laurylalcohol-diglycolethersulfate-sodium salt, 28% aqueous solution |
| 15.0 g | isopropylalcohol |
| 0.03 g | ammonia, 25% |
| 79.27 g | water |
| 100.00 g | | is applied onto white human hair and allowed to work itself in for a period of 10 minutes. After rinsing with water and then drying the hair is colored bright red.

Example 2

Color strengthener

| | |
|---|---|
| 0.10 g | 1-amino-4-(2',3'-dihydroxypropyl)-amino-5-chloro-2 nitrobenzene |
| 2.00 g | polyvinylpyrrolidone |
| 0.10 g | glycerin |
| 40.00 g | isopropyl alcohol |
| 57.80 g | water |
| 100.00 g | |

White human hairs soaked with the strengthening coloring solution are arranged into a hairdo and dried. The hair is colored bright red and strengthened.

Example 3

Oxidation Hair Coloring Composition

| | |
|---|---|
| 0.2 g | 4-amino-1(2',3'-dihydroxpropyl)-amino-5-chloro-2-nitrobenzene |
| 35.0 g | oleic acid |
| 15.0 g | isopropyl alcohol |
| 18.0 g | ammonia, 25% |
| 0.2 g | disodium salt of ethylene diamine |
| 0.1 g | sodium sulfate |
| 0.8 g | p-toluylenediamine-sulfate |
| 0.2 g | resorcin |
| 0.05 g | m-aminophenol |
| 30.45 g | water |
| 100.00 g | |

50 ml of this hair coloring composition are mixed shortly before use with 50 ml hydrogen peroxide solution (6%). The gel produced is subsequently applied to gray human hair and allowed to work in for a period of 30 minutes. Thereafter follows rinsing with water and drying. The hair has obtained a reddish-blonde coloration.

Example 4

Hair Strengthener:

| | |
|---|---|
| 0.15 g | 4-amino-1-(2',3'-dihydroxypropyl)-amino-5-chloro-2-nitrobenzene |
| 2.0 g | copolymerizate of vinylpyrrolidone vinylacetate 60:40 |
| 0.1 g | glycerin |
| 40.0 g | isopropyl alcohol |
| 57.75 g | water |
| 100.00 g | |

White human hair is arranged with this strengthening coloring solution into a hairdo, and subsequently dried. The hairs are colored bluish-red and strengthened.

Example 5

A liquid hair coloring composition composed of

| | |
|---|---|
| 0.1 g | 4-amino-1-(2',3'-dihydroxypropyl)-amino-5-chloro-2-nitrobenzene |
| 5.0 g | laurylalcohol-diglycolethersulfate-sodium salt, 28% aqueous solution |
| 0.5 g | hydroxyethylcellulose |
| 15.0 g | ethylalcohol |
| 0.03 g | ammonia, 25% |
| 79.37 g | water |
| 100.00 g | | is applied onto white human hair and left to act, i.e. work itself in for 10 minutes. It is then rinsed with water, followed by drying of the hair. The hair has obtained a bluish-red coloration.

Example 6

A liquid hair coloring composition,

| | |
|---|---|
| 0.1 g | 4-amino-1-(2'3'-dihydroxypropyl)-amino-5-chloro-2-nitrobenzene |
| 0.5 g | hydroxyethylcellulose |
| 5.0 g | laurylalcohol-diglycolethersulfate-sodium salt, 28% |
| 15.0 g | isopropylalcohol |
| 0.3 g | Acid Brown 4 (C.I. 14 805) |
| 0.03 g | ammonia, 25% |
| 79.07 g | water |
| 100.00 g | | is applied onto white human hair and allowed to work itself in i.e. penetrate for 10 minutes. After rinsing with water and drying, the hair is colored red-brown.

Example 7

A liquid hair coloring composition, ingredients

| | |
|---|---|
| 0.1 g | 1-(2'-hydroxyethyl)-amino-4-(2',3'-dihydroxypropyl)-amino-5-chloro-2-nitrobenzene |
| 0.5 g | hydroxyethylcellulose |
| 5.0 g | laurylalcohol-diglycoethersulfate-sodium salt, 28% aqueous solution |
| 15.0 g | isopropylalcohol |
| 0.03 g | ammonia, 25% |
| 79.37 g | water | is applied onto white human hair and left thereon for a period of 10 minutes. After rinsing with water and drying, the hair is colored violet.

Example 8

Hair Strengthener

| | |
|---|---|
| 0.15 g | 1-(2'-hydroxyethyl)-amino-4-(2',3'-dihydroxypropyl)-amino-5-chloro-2-nitrobenzene |
| 2.00 g | polyvinylpyrrolidone |
| 0.10 g | glycerin |
| 40.00 g | isopropyl alcohol |
| 57.75 g | water |
| 100.00 g | |

White human hair is set into a hairdo with the coloring solution described above, and then dried. The hair is colored violet and strengthened.

Example 9

Oxidation Composition

| | |
|---|---|
| 0.2 g | 1,4-di-[(2',3'-dihydroxypropyl)-amino]-5-chloro-2-nitrobenzene |
| 35.0 g | oleic acid |
| 15.0 g | isopropylalcohol |
| 18.0 g | ammonia, 25% |
| 0.2 g | disodium salt of ethylenediamine tetraacetic acid |
| 0.1 g | sodium sulfite |
| 0.8 g | p-toluylenediamine-sulfate |
| 0.2 g | resorcin |
| 0.05 g | m-aminophenol |
| 30.45 g | water |
| 100.00 g | |

50 ml of this hair coloring composition are mixed with 50 ml hydrogen peroxide solution (6%) shortly before use. The resulting gel is then applied onto grey human hair and left thereon for a period of 30 minutes. It is then rinsed with water and dried. The hair has obtained a reddish-blonde coloration.

Example 10

A liquid hair coloring composition, ingredients

| | |
|---|---|
| 0.7 g | 1-amino-4-(2',3'-dihydroxypropyl)-amino-5-chloro-2-nitrobenzene |
| 0.3 g | 1,4-di-[(2',3'-dihydroxypropyl)-amino]-5-chlor-2-nitrobenzene |
| 0.5 g | hydroxyethylcellulose |
| 5.0 g | laurylalcohol-diglycolethersulfate-sodium salt, 28% aqueous solution |
| 15.0 g | isopropylalcohol |
| 0.05 g | ammonia, 25% |
| 78.45 g | water |
| 100.00 g | | is applied onto white human hair and allowed to react for 15 minutes. After rinsing with water and drying, the hair is colored dark red-violet.

PREPARATION EXAMPLES

The following examples illustrate preparation of compounds employed in hair coloring compositions according to the present invention.

Example 11

1-amino-4-(2',3'-dihydroxypropyl)-amino-5-chloro-2-nitrobenzene 18.7 g (0.1 Mol) 1,4-diamino-5-chloro-2-nitrobenzene are dissolved in 40 ml dimethylformamide reacted with 44.0 g chloropropanediol-(2,3). After heating to 150° C. (oil bath temperature) a solution of 20.0 g sodium hydroxide in 200 ml water is added dropwise within 2½ hours. After cooling, the reaction mixture is extracted with methylene chloride, whereby the dimethylformamide and excess chloropropanediol act as dissolving intermediary for the dihydroxypropyl compound. The methylenechloride is evacuated in a vacuum. Upon subsequent addition of water to the residue, the 1-amino-4-(2',3'-dihydroxypropyl)-amino-5-chloro-2-nitrobenzene crystallizes out. After recrystallization from water, the compound melts at 126° C.

Yield: 5.0 g

| Infrared Absorption bands (cm$^{-1}$): | | |
|---|---|---|
| 3000–3600 (broad) | 1414 | 1020 |
| 1563 | 1327 | 995 |
| 1520 | 1222 (broad) | 860 |
| 1480 | 1115 | 760 |

Example 12

4-amino-1-(2',3'-dihydroypropyl)-amino-5-chloro-2-nitro benzene 2.49 g (0.01 Mol) 2 nitro-4-acetylamino-1,5-dichlorobenzene are dissolved in 18 ml 2-methoxy-ethanol and heated with 5.4 g (0.06 Mol) 1-aminopropanediol-(2,3) for 4 hours to 150° C. (oil bath temperature). After cooling, the acetyl compound precipitates out upon standing longer. It is then evaporated in a vacuum, saponified with alcoholic hydrochloric acid, and the base is precipitated with ammonia. The compound is recrystallized from ethyl acetate and melts at 162° C.

Yield: 0.5 g

| Infrared Absorption bands (cm$^{-1}$) | | |
|---|---|---|
| 3000–3600 (broad) | 1510 sh | 1195 |
| 1625 | 1411 | 1024 |
| 1562 | 1314 | 998 |
| 1515 | 1240 | |

Example 13

1-(2'-hydroxyethyl)-amino-4-(2',3'-dihydroxypropyl-)amino-5-chloro-2-nitrobenzene 2.3 g (0.01 Mol) 1-(2'hydroxethyl)-amino-4-amino-5-chloro-2-nitrobenzene are heated with 5 ml H$_2$O and 5.5 g chloropropanediol-(2,3). (0.05 Mol) to 130° C. (oil bath temperature) then 1.25 g sodiumhydroxide in 12.5 ml H$_2$O are added dropwise. After 30 minutes the reaction is finished. The substance precipitates out upon cooling. It is then recrystallized from water, yielding 1.2 g of the desired compound, melting point 172° C.

| Infrared Absorption bands (cm$^{-1}$) | | |
| --- | --- | --- |
| 3000–3600 (broad) | 1335 | 1000 |
| 1565 | 1195 | 860 |
| 1525 | 1048 | 755 |
| 1405 | 1025 | |

Example 14
1,4-di[(2',3'-dihydroxypropyl)-amino]-5-chloro-2-nitrobenzene 18.7 g (0.1 Mol) 1,4-diamino-5-chloro-2-nitrobenzene and 22 g (0.1 Mol) 3-chloroprpanediol-(1,2) are heated in 20 ml water to 150° C. (oil bath temperature). With stirring is added dropwise a solution of 8 g sodiumhydroxide in 80 ml water during 1 hour and the reaction mixture is kept 1 hour more at 150° C. It is then diluted with water. Upon cooling there precipitates a mixture of 1-amino-4-(2',3'-dihydroxypropyl)-amino-5-chloro-2-nitrobenzene and 1,4-di[(2',3'-dihydroxypropyl)-amino]-5-chloro-2-nitrobenzene. The sediment is then evacuated in a vacuum and dried. Yield: 14 g of an approximately 1:1 mixture of both compounds.

The mixture is recrystallized from 220 ml n-butanol for separation. The 1,4-di-[(2',3'-dihydroxypropyl)-amino]-5-chloro-2-nitrobenzene crystallizes out, while the monoalkyl compound remains in solution. Repeated recrystallization produces the pure dialkyl compound in crystals of melting point 208° C.

| Infrared Absorption bands (cm$^{-1}$) | | |
| --- | --- | --- |
| 3000–3600 (broad) | 1330 | 1020 |
| 1635 | 1230 | 995 |
| 1565 | 1200 | 862 |
| 1525 | 1110 | 760 |
| 1405 | 1075 | |

The monoalkyl compound can be recovered similarly pure, by distilling off of the n-butanol and multiple recrystallization from water.

All of the percents recited herein are percent by weight.

While the invention has been described and illustrated as embodied in 1,4-diamino-5-chloro-2-nitrobenzene derivatives, processes for their production and compositions containing the same for coloration of hair, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to protected by letters patent is set forth in the appended claims.

We claim:
1. 1,4-diamino-5-chloro-2-nitrobenzene of the general formula I

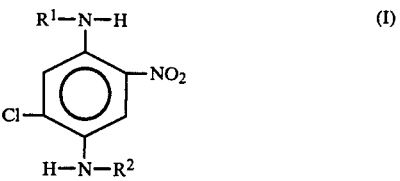

wherein $R^1$ and $R^2$ are the same or different and are each hydrogen, 2-hydroxyethyl or 2,3-dihydroxypropyl, with the proviso that at least one of said $R^1$ and $R^2$ is 2,3-dihydroxypropyl.

2. The compound according to claim 1, 1-amino-4-(2',3'-dihydroxypropyl)amino-5-chloro-2-nitrobenzene.

3. The compound according to claim 1, 4-amino-1-(2',3'-dihydroxypropyl)-amino-5-chloro-2-nitrobenzene.

4. The compound according to claim 1, 1-(2'-hydroxyethyl)-amino-4-(2',3'-dihydroxypropyl)-amino-5-chloro-2-nitrobenzene.

5. The compound according to claim 1, 1,4-di-[(2',3'-dihydroxypropyl)-amino]-5-chloro-2-nitrobenzene.

6. Composition for the coloration of hair, comprising at least one compound according to claim 1 in mixture with cosmetic additive carrier means.

7. The composition according to claim 6 for the dyeing of hair without oxidation means, said compound according to formula I being present in a concentration between about 0.01 and 2.0 percent by weight.

8. The composition according to claim 6 for the dyeing of hair without oxidation means, wherein said compound of formula I is present in a concentration between about 0.01 and 1.0 percent by weight.

9. The composition according to claim 6, wherein a total content of dye lies within the limits between about 0.01 and 3.0 percent by weight.

10. The composition according to claim 6, for the dyeing of hair without oxidation means, having a pH-value within the range from 7 up to 10.5.

11. The composition according to claim 6, for the dyeing of hair without oxidation means, having a pH-value within the range from 7.5 up to 9.5.

12. The composition according to claim 6, for the dyeing of hair with oxidation means, further comprising at least one known oxidation hair dye.

13. The composition according to claim 6, for the dyeing of hair with oxidation means, further comprising for additional hair strengthening known direct-drawing on the hair dye means in aqueous-alcoholic soultion and at least one known cosmetic polymerizate.

14. The composition according to claim 6, for the dyeing of hair with oxidation means, having a pH-value between 8.0 and 11.5 adjusted by means of ammonia or organic amine.

15. The composition according to claim 14, wherein said organic amine is selected from the group consisting of monoethanol amine and triethanolamine.

16. The composition according to claim 6, for the dyeing of hair with oxidation means, containing oxidation means in a concentration between about 0.01 and 2.0 percent by weight.

17. The composition according to claim 16, wherein said oxidation means concentration is between 0.05 and 1.0 percent by weight.

18. The composition according to claim 16, having a total content of dye between about 0.1 and 5.0 percent by weight.

19. Method for the coloration of human hair without oxidation means, comprising applying onto the hair a hair coloring effective amount of the composition according to claim 6, leaving said composition on said hair for a period between 5 and 30 minutes, rinsing with water, with or without further rinsing with a weak organic acid, and then drying.

20. Method for the coloring of human hair with oxidation means, comprising mixing the composition according to claim 12 with oxidation means, applying onto said hair a hair coloring effective amount of said mixture, leaving said mixture on said hair for a period from 10 to 45 minutes, rinsing with water, with or without further rinsing with a weak organic acid, and drying.

* * * * *